US00PP27817P3

(12) United States Plant Patent
Klemm et al.

(10) Patent No.: US PP27,817 P3
(45) Date of Patent: Mar. 28, 2017

(54) ***DIANTHUS* PLANT NAMED 'KLEDP15181'**

(50) Latin Name: *Dianthus caryophyllus*
Varietal Denomination: KLEDP15181

(71) Applicant: Klemm+Sohn GmbH & Co. KG, Stuttgart (DE)

(72) Inventors: Nils Klemm, Stuttgart (DE); Martin Glawe, Stuttgart (DE); Lena Gutbrodt, Bempfingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 71 days.

(21) Appl. No.: 14/545,534

(22) Filed: May 18, 2015

(65) Prior Publication Data

US 2016/0345481 P1 Nov. 24, 2016

(51) Int. Cl.
*A01H 5/02* (2006.01)

(52) U.S. Cl.
USPC ..... Plt./276

(58) Field of Classification Search
USPC ..... Plt./276
See application file for complete search history.

*Primary Examiner* — Anne Grunberg
(74) *Attorney, Agent, or Firm* — Bethany R. Roahrig; James M. Weatherly; Cochran Freund & Young, LLC

(57) ABSTRACT

A new *dianthus* plant particularly distinguished by having light pink flowers with a pink star, good branching, and medium vigor, is disclosed.

1 Drawing Sheet

Genus and species: *Dianthus caryophyllus*.
Variety denomination: 'KLEDP15181'.

BACKGROUND OF THE NEW PLANT

The present invention comprises a new and distinct variety of *dianthus*, botanically known as *Dianthus caryophyllus* and hereinafter referred to by the variety name 'KLEDP15181'. 'KLEDP15181' was a newly found whole plant mutation of 'Oscar Pink and Purple' (unpatented) identified in March 2010 in Stuttgart, Germany in a greenhouse.

In July of 2010 'KLEDP15181' was first vegetatively propagated by vegetative cuttings. 'KLEDP15181' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Light pink flowers with a pink star;
2. Good branching; and
3. Medium vigor.

CROSS REFERENCE TO RELATED APPLICATIONS

Plant Breeder's Rights for 'KLEDP15181' were applied for in Canada on Apr. 2, 2015 (Application number 15-8576). 'KLEDP15181' has not been made publicly available or sold more than one year prior to the filing date of this application.

DESCRIPTION OF THE PHOTOGRAPH

This new *Dianthus* plant is illustrated by the accompanying photograph which shows an overall view of the plant.

The colors shown are as true as can be reasonably obtained by conventional photographic procedures.

The photograph is of a plant that is about 3 months-old grown in Stuttgart, Germany in May 2014.

DESCRIPTION OF THE NEW VARIETY

The following detailed descriptions set forth the distinctive characteristics of 'KLEDP15181'. The data which define these characteristics were collected from asexual reproductions carried out in Stuttgart, Germany. Data was collected on 22 week-old plants grown in a greenhouse in Stuttgart, Germany in April 2015. Color references are to The R.H.S. Colour Chart of The Royal Horticultural Society of London (R.H.S.), 5$^{th}$ edition (2007).

Classification:
- *Family.*—*Caryophyllaceae.*
- *Species.*—*Dianthus caryophyllus.*
- *Common name.*—Pot carnation.
- *Variety.*—'KLEDP15181'.

Parentage:
- *Mutation of 'Oscar Pink and Purple'* (*unpatented*).

Propagation:
- *Type.*—Vegetative stem cuttings.
- *Time to produce a rooted young plant.*—14 to 16 days.
- *Root description.*—White, fine.
- *Rooting habit.*—Lanceolate.

Plant description:
- *Plant form.*—Potted plant, upright.
- *Plant height.*—13.0 cm to 15.0 cm.
- *Plant diameter or spread.*—16.0 cm to 20.0 cm.

Lateral branches:
- *Stem.*—Solid.
- *Length.*—8.0 cm to 10.0 cm.
- *Diameter.*—0.3 cm to 0.5 cm.
- *Number of internodes per stem.*—4 to 5.
- *Internode length.*—2.0 cm to 3.0 cm.
- *Node length.*—0.3 cm to 0.4 cm.

*Node diameter.*—0.4 cm.
*Texture.*—Smooth.
*Color.*—RHS 138A.

Foliage description:
*Arrangement.*—Opposite.
*Length.*—4.0 cm to 6.0 cm.
*Width.*—0.6 cm to 0.8 cm.
*Shape.*—Lanceolate.
*Apex.*—Acute.
*Base.*—Obtuse.
*Margin.*—Entire.
*Texture* (*both surfaces*).—Smooth.
*Venation pattern.*—Mainly parallel.
*Color.*—Immature leaves: Upper surface: RHS 137B. Lower surface: RHS 138A. Mature leaves: Upper surfaces: RHS 139A. Lower surface: RHS 137A. Venation: RHS 139A.

Flower description:
*Flower type and habit.*—Round, double, small sprays.
*Flower position.*—Slightly above the foliage.
*Fragrance.*—Present.
*Natural flowering season.*—Spring to fall.
*Flower longevity.*—10 to 14 days.
*Number of flowers per spray.*—3 to 5.
*Flower buds.*—Length: 1.5 cm to 2.0 cm. Diameter: 0.8 cm to 1.0 cm. Shape: Elliptic. Color: RHS 138A and RHS 143B. Extrusion of the styles at bud stage: Absent.
*Corolla.*—Quantity of petals/arrangement: 18 to 22, arranged in several whorls. Corolla height: 1.5 cm to 2.0 cm. Petal length: 3.0 cm. Petal width: 1.5 cm to 2.0 cm. Petal shape: Spoon shaped. Petal apex: Obtuse. Petal base: Acute. Petal margin: Crenate, depth is medium. Petal texture (both surfaces): Smooth. Petal color immature and mature: Upper surface: The secondary color in the eye is RHS 50A and the main color is RHS 56A. Lower surface: RHS 56D. Calyx: Quantity of sepals/arrangement: 4 to 5, fused. Calyx height: 1.8 cm to 2.0 cm. Calyx diameter, at the apex: 0.8 cm to 1.0 cm. Shape: Campanulate. Sepal apex shape: Acute. Sepal texture (both surfaces): Smooth. Sepal color: Upper surface: RHS 138B and RHS 143A. Lower surface: RHS 144B. Epicalyx: Position of the outer lobes in relation to the calyx: Adpressed. Apex shape of inner and outer lobes: Acute. Length: 0.8 cm.

Peduncles:
*Length.*—10.0 cm to 14.0 cm.
*Diameter.*—0.2 cm.
*Strength.*—Moderate.
*Texture.*—Smooth.
*Color.*—RHS N137B.

Reproductive organs:
*Stamens.*—Quantity: Moderate. Filament length: 0.4 cm to 0.6 cm. Filament color: RHS 155B. Anther length: 0.1 cm. Anther diameter: 0.05 cm. Anther color: RHS 19B. Pollen amount: Sparse.
*Pistils.*—Quantity: 1. Pistil length: 0.1 cm. Style length: 1.6 cm to 1.8 cm. Style color: RHS 59A. Stigma shape: Filamentous. Stigma color: RHS 59A. Ovary size: 0.4 cm to 0.6 cm. Ovary shape: Oval. Ovary color: RHS 145A. Ovary texture: Smooth.

Fruit and seed: None observed.

Disease and insect/pest resistance: No special observations were made.

COMPARISON WITH PARENTAL LINES AND KNOWN VARIETY

'KLEDP15181' is a distinct variety of *dianthus*. 'KLEDP15181' is distinguished from its parent as described in Table 1:

TABLE 1

Comparison with Parental Line

| Trait | Variety 'KLEDP15181' | Parent 'Oscar Pink and Purple' |
|---|---|---|
| Flower color | Light pink with pink star | Pink with purple eye |

'KLEDP15181' is most similar to the commercial *dianthus* plant named 'Oscar' also known as 'KLEDP07089' (unpatented). Differences between the two varieties are described in Table 2:

TABLE 2

Comparison with Similar Variety

| Trait | Variety 'KLEDP15181' | Commercial line 'Oscar' |
|---|---|---|
| Flower color | Light pink with pink star | Pink with purple eye |

We claim:

1. A new and distinct variety of *dianthus* plant named 'KLEDP15181' as illustrated and described herein.

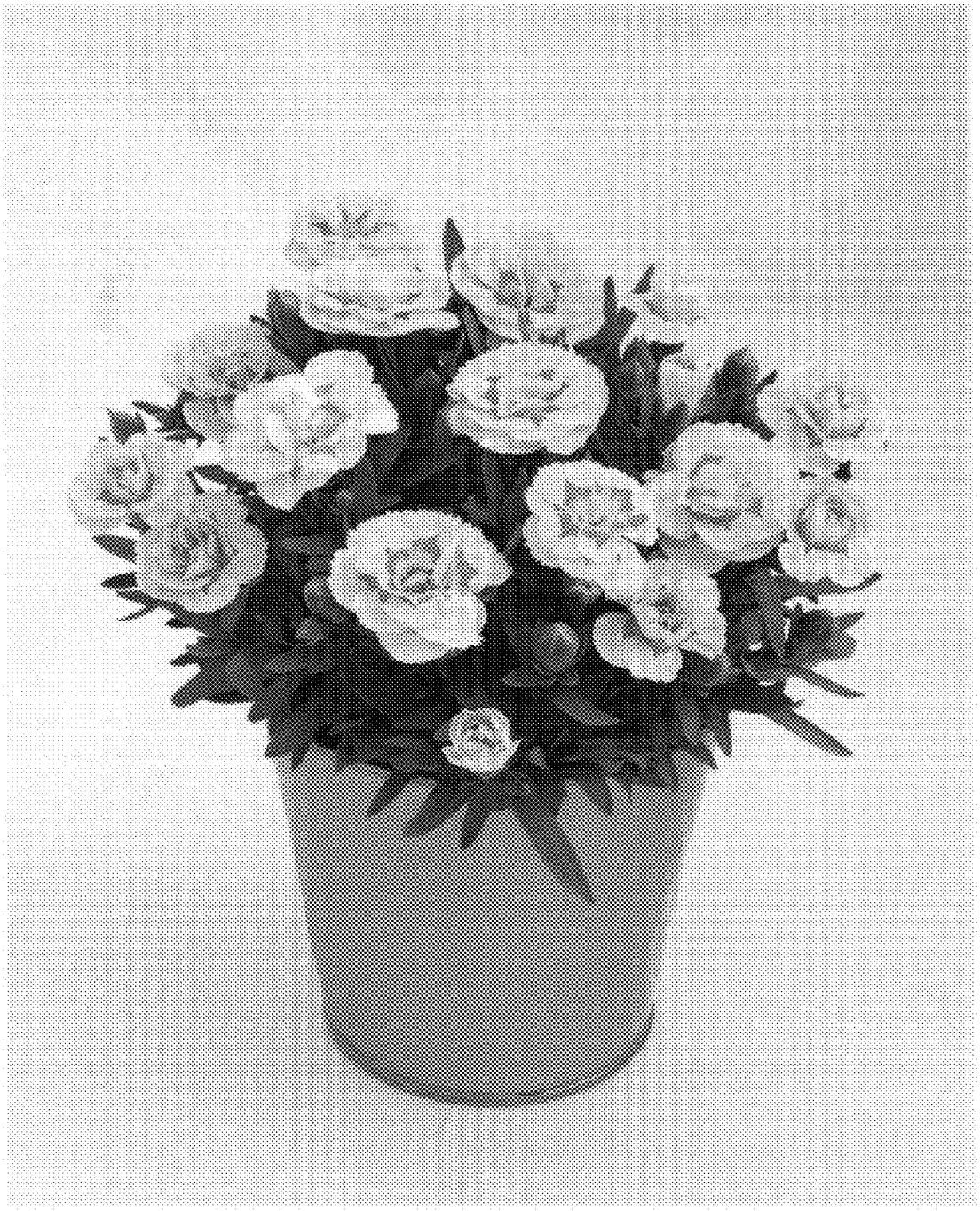

* * * * *